US008840570B2

(12) United States Patent
Branch et al.

(10) Patent No.: US 8,840,570 B2
(45) Date of Patent: Sep. 23, 2014

(54) MULTI-SECTION LIMB AND LIGAMENT EVALUATION APPARATUS AND ASSOCIATED METHODS FOR USING SAME

(75) Inventors: Thomas P. Branch, Atlanta, GA (US); Alexander Sattler, Jr., Marietta, GA (US); Eric Kenneth Branch, Weston, FL (US); Cale Andrew Jacobs, Suwanee, GA (US)

(73) Assignee: Ermi, Inc., Atlanta, GA (US)

( * ) Notice: Subject to any disclaimer, the term of this patent is extended or adjusted under 35 U.S.C. 154(b) by 722 days.

(21) Appl. No.: 12/267,109

(22) Filed: Nov. 7, 2008

(65) Prior Publication Data
US 2009/0124936 A1 May 14, 2009

Related U.S. Application Data

(60) Provisional application No. 60/986,903, filed on Nov. 9, 2007.

(51) Int. Cl.
*A61B 5/103* (2006.01)
*A61B 5/11* (2006.01)
*A61B 5/00* (2006.01)

(52) U.S. Cl.
CPC .............. *A61B 5/1121* (2013.01); *A61B 5/4585* (2013.01); *A61B 5/1124* (2013.01); *A61B 5/4528* (2013.01); *A61B 5/4533* (2013.01); *A61B 5/6828* (2013.01)
USPC ............................ 600/587; 600/592; 600/595

(58) Field of Classification Search
CPC ...... A61B 5/45; A61B 5/4504; A61B 5/4514; A61B 5/4519; A61B 5/4523; A61B 5/4528; A61B 5/4533; A61B 5/4538; A61B 5/4585; A61B 5/4595
USPC ............... 128/845, 882; 482/131; 5/624, 648, 5/650, 651; 600/587, 592, 595; 601/5, 601/34, 35
See application file for complete search history.

(56) References Cited

U.S. PATENT DOCUMENTS

T100,602 I4 * 5/1981 Roley et al. .................... 600/595
4,407,277 A * 10/1983 Ellison ............................ 602/39

(Continued)

FOREIGN PATENT DOCUMENTS

| CA | 2615171 A1 | 1/2007 |
| DE | 36 09 535 A1 | 9/1987 |

(Continued)

OTHER PUBLICATIONS

Invitation to Pay Additional Fees and, where Applicable, Protest Fee Search Report for International Application No. PCT/US20008/012578 received Apr. 17, 2009.

(Continued)

*Primary Examiner* — Max Hindenburg
*Assistant Examiner* — John Pani
(74) *Attorney, Agent, or Firm* — Gronholm Patent Services

(57) ABSTRACT

A method and apparatus for reliably positioning a 3-segment limb, such as a leg or arm for imaging and medical analysis, which can accommodate for the patient's "natural alignment". The apparatus positions the limb in such a way that the position of the proximal segment is controlled while an known external torque is applied at a known rate to the distal segment. The location of each of the limb's three segments is recorded using either external or internal measurement techniques, and the relative motions between the proximal and intermediate segments are used in the orthopedic evaluation of the proximal joint. Furthermore, the relative motions between the intermediate and distal segments are used in the orthopedic evaluation of the distal joint. By applying a known torque at a known rate, clinicians will be provided with valuable information related to joint range of motion, stability, laxity, and compliance.

7 Claims, 12 Drawing Sheets

(56) References Cited

U.S. PATENT DOCUMENTS

| | | | |
|---|---|---|---|
| 4,586,495 A | | 5/1986 | Petrofsky |
| 4,650,183 A | | 3/1987 | McIntyre |
| 4,727,860 A | | 3/1988 | McIntyre |
| 4,733,859 A | | 3/1988 | Kock et al. |
| 4,771,548 A | * | 9/1988 | Donnery .................. 33/512 |
| 4,823,807 A | | 4/1989 | Russell et al. |
| 4,825,852 A | | 5/1989 | Genovese et al. |
| 4,834,073 A | | 5/1989 | Bledsoe et al. |
| 4,909,262 A | | 3/1990 | Halpern et al. |
| 4,930,497 A | | 6/1990 | Saringer |
| 5,027,799 A | | 7/1991 | Laico et al. |
| 5,056,535 A | * | 10/1991 | Bonnell .................. 128/882 |
| 5,211,161 A | * | 5/1993 | Stef ........................ 601/5 |
| 5,228,432 A | | 7/1993 | Kaiser et al. |
| 5,335,674 A | | 8/1994 | Siegler |
| 5,382,225 A | | 1/1995 | Sutcliffe |
| 5,399,147 A | * | 3/1995 | Kaiser ..................... 601/34 |
| 5,402,800 A | | 4/1995 | Hollis |
| 5,435,321 A | | 7/1995 | McMillen et al. |
| 5,645,079 A | | 7/1997 | Zahiri |
| 6,599,255 B2 | | 7/2003 | Zhang |
| 6,669,660 B2 | | 12/2003 | Branch |
| 6,821,231 B1 | * | 11/2004 | Hall ........................ 482/51 |
| 6,872,186 B2 | | 3/2005 | Branch et al. |
| 7,041,069 B2 | | 5/2006 | West |
| 7,479,121 B2 | | 1/2009 | Branch |
| 7,547,289 B2 | | 6/2009 | Branch |
| 7,628,766 B1 | | 12/2009 | Kazerooni et al. |
| 7,665,167 B2 | | 2/2010 | Branch et al. |
| 7,854,685 B2 | | 12/2010 | Cole et al. |
| 7,951,097 B2 | | 5/2011 | Schaeffer |
| 7,985,227 B2 | | 7/2011 | Branch et al. |
| 2004/0260208 A1 | | 12/2004 | Laprade et al. |
| 2005/0222573 A1 | | 10/2005 | Branch et al. |
| 2006/0064048 A1 | * | 3/2006 | Stano ...................... 602/28 |
| 2006/0097557 A1 | * | 5/2006 | Tholkes et al. ............. 297/330 |
| 2007/0123997 A1 | | 5/2007 | Herr et al. |
| 2010/0179605 A1 | | 7/2010 | Branch et al. |
| 2012/0046540 A1 | | 2/2012 | Branch et al. |

FOREIGN PATENT DOCUMENTS

| | | |
|---|---|---|
| DE | 39 25 014 A1 | 1/1991 |
| EP | 0204639 A2 | 12/1986 |
| EP | 1 219 240 A | 7/2002 |
| WO | WO 8804536 A1 | 6/1988 |
| WO | WO 9302621 A1 | 2/1993 |
| WO | WO 02/096274 A | 12/2002 |
| WO | WO 2007/009063 A2 | 1/2007 |

OTHER PUBLICATIONS

Shultz Sandra, J., et al., "Measurement of varus-valgus and internal-external rotational knee laxities in vivo—Part I: assessment of measurement reliability and bilateral asymmetry," Journal of Orthopaedic Research: Official Publication of the Orthopaedic Research Society, Aug. 2007, vol. 25, No. 8, XP002515908, ISSN: 0736-0266, p. 981-p. 988.

Shino, K. et al., "Measurement of anterior instability of the knee. A new apparatus for clinical testing," The Journal of Bone and Joint Surgery, British Volume, Aug. 1987, vol. 69, No. 4, XP002515908; ISSN: 0301-620X, p. 608-p. 613.

Van Der Esch, M. et al., "Reproducibility of instrumented knee joint laxity measurement in healthy subjects," Rheumatology (Oxford, England) May 2006, vol. 45, No. 5, pp. 595-599, XP002515910; ISSN: 1462-0324.

Uh B.S., et al., "A new device to measure knee laxity during weightbearing and non-weightbearing conditions," Journal of Orthopaedic Research: Official Publication of the Orthopaedic Research Society Nov. 2001, vol. 19, No. 6, XP002515911; ISSN: 0736-0266, p. 1185-p. 1191.

Markolf, K. L., et al., "In vivo knee stability. A quantitative assessment using an instrumented clinical testing apparatus," Journal of Bone and Joint Surgery, American Volume Jul. 1978, vol. 60, No. 5, XP002515912, ISSN: 0021-9355, p. 654-p. 674.

Dale M. Daniel, M.D., "MEDmetric® Knee Ligament Arthrometer Models KT1000™ and KT2000™," Reference, Maintenance & User Guide for the Knee Ligament Arthrometer®, First Edition, May 1993, Revised Dec. 1993; May 1994, Jul. 1994; Oct. 1996; Dec. 1998, 51 pgs, San Diego, CA.

B.D. Beynnon et al., "The Effect of Functional Knee-Braces on Strain on the Anterior Cruciate Ligament in Vivo," Journal of Bone and Joint Surgery; Boston, US; vol. 74A, No. 9; Oct. 1, 1992; pp. 1298-1312; XP000322579.

S.C. Shoemaker et al., "In-Vivo Rotatory Knee Stability Ligamentous and Muscular Contributions," Journal of Bone and Joint Surgery; Boston, US; vol. 64, No. 2; 1982; pp. 208-216; XP008050394.

Li-Wun Zhang et al., "Dynamic and Static Properties of The Human Knee Joint in Axial Rotation," Engineering in Medicine and Biology Society, 1997, Proceedings of the 19th Annual International Conference of the IEEE Chicago, IL, USA Oct. 30-Nov. 2, 1997; Piscataway, NJ, USA, IEEE, US; vol. 4.

Roley et al., "T100,602—Apparatus for Measuring Angles," United States Defensive Publication, May 5, 1981; 5 pages.

International Search Report for International Application No. PCT1US20061027376 filed Apr. 19, 2007.

Medmetric Corporation, "In These Times of Managed Care, Measured Outcomes are Crucial," found at http://web. archive.org/web120040610111553/http://medmetric.com (1 page).

Medmetric Corporation, "KT100/S;" found at http://web.archive.org/web/20040628060104/www.kt1000.com/kts.htm (2 pages).

Medmetric Corporation, "KT2000," found at http://web.archive.org/web/20040618192953/www.kt1000.com/kts.htm (2 pages).

International Search Report from corresponding International Application No. PCT/US2008/012578 received Aug. 11, 2009.

Notice of Allowance dated Mar. 9, 2010, U.S. Appl. No. 11/457,443, filed Jul. 13, 2006.

Office Action dated Aug. 6, 2009, U.S. Appl. No. 11/457,443, filed Jul. 13, 2006.

International Preliminary Examining Authority, Written Opinion for International Application No. PCT/US2011/047696, mailed Aug. 3, 2012, 8 pages, European Patent Office, The Netherlands.

United States Patent and Trademark Office, Office Action for U.S. Appl. No. 12/797,324, dated Oct. 1, 2012, 9 pages, USA.

European Patent Office, Office Action dated Apr. 4, 2012, for Application No. EP06787304.2.

Office Action dated Dec. 9, 2011 in U.S. Appl. No. 12/797,324, filed Jun. 9, 2010.

United States Patent and Trademark Office, Office Action for U.S. Appl. No. 13/209,380, Jun. 4, 2013, 29 pags, USA.

European Patent Office, Jun. 12, 2014 Communication pursuant to Article 94(3) EPC, application No. 08 849 187.3 (6 pages total).

* cited by examiner

MULTI-SECTION LIMB AND LIGAMENT EVALUATION APPARATUS AND ASSOCIATED METHODS FOR USING SAME

CROSS-REFERENCE TO RELATED APPLICATIONS

This application claims priority to and the benefit of U.S. Provisional Application No. 60/986,903, filed Nov. 9, 2007, entitled "Ligament Evaluation Apparatus and Associated Methods," which is incorporated herein in its entirety, including its appendix.

FIELD OF THE INVENTION

The present invention relates to apparatuses and methods for evaluating the performance of a joint. More particularly, the present invention provides apparatus and methods for quantifying the amount of movement allowed by a joint to aid in the diagnosis of and treatment for ligament damage.

BACKGROUND OF THE INVENTION

The knee is composed of the femur or thigh bone, the tibia or shin bone and the patella or knee cap. They are connected by fibrous structures called ligaments which allow a certain amount of 'joint play' to exist between the bone structures. When this 'joint play' is increased or decreased an abnormal or pathological condition exists in the knee. Attempts have been made in the past to quantify this increase or decrease in 'joint play' of the knee with limited success.

An injury to the knee can cause damage to one or more of the structures of the knee causing an increase in the 'joint play' of the knee. This increase in 'joint play' can create the sensation to the patient that the knee is slipping or 'coming out of joint'. Commonly, this sensation described by the patient is referred to as the feeling of 'joint instability'. The ability of the two bones to actually 'come out of joint' is related to the length of the fibrous structures or ligaments which connect the two bones together as well as the shape and size of the two bones (or three). The ability of the bones to 'come out of joint' or become unstable is related to the amount of stretch or the amount of increased lengthening of each ligament, the number of ligaments involved, and damage to other support structures of the knee such as the bone itself and the menisci. Accurate measurement of this increased ligament length can be critical to restore the knee to as close to its original functional and anatomical state as possible.

Currently, there are only manual tests used by clinicians to aid in the diagnosis of ligament damage or increased (decreased) joint play. As an example, there are three manual tests to evaluate the increased joint play associated with an ACL tear—the Lachman's test, the Pivot Shift test and the Anterior Drawer Test. All of these tests suffer from the clinician's subjective evaluation of both the extent of the ligament lengthening and the change in the compliance or stretchiness of the ligament.

The Lachman's test is performed by laying the patient in a supine position and bending the knee at approximately 20 to 30 degrees. The clinician places a hand on the patient's upper thigh and his other hand below the upper part of the patient's calf muscle. Pressure is applied under the patient's calf and down on the patient's thigh such that translation between the tibia and femur occurs.

Similar to the Lachman's test, the pivot shift test begins by positioning the patient on his back. The knee is flexed (x-axis rotation) and a valgus (z-axis rotation) force and an internal rotation (y-axis rotation) force is applied to the knee as the knee is brought into full extension (x-axis rotation). The clinician feels for an abnormal internal rotation (y-axis rotation) and anterior translation (z-axis translation) of the tibia with respect to the femur. This shift is felt to represent the relative increased translation (z-axis translation) of the lateral side of the knee with respect to the increased translation (z-axis translation) of the medial side of the knee. Furthermore, the point of sudden shift represents the point at which the back part of the tibia bone slides in front of the radius of curvature of the curved end of the femur. The clinician subjectively rates the pivot shift as Grade I, Grade II or Grade III depending upon the degree of rotational and translational shift felt during the test. This test is difficult to perform, difficult to teach and difficult to quantify.

Finally, the anterior drawer test is performed with the patient lying on his back and his knee bent to 90 degrees. With the patient's foot supported by a table or chair, the clinician applies pressure to the knee using her thumbs. This test is graded based upon the amount or extent of anterior translation along the z-axis of the tibia with respect to the femur. Grade I has 0 to 5 mm of anterior translation (z-axis translation), Grade II has 6 to 10 mm of anterior translation, and Grade III has 11 to 15 mm of translation.

To diagnose an injured ACL using the described tests, the clinician must determine whether the knee feels "abnormal." Thus, the accuracy of an ACL injury diagnosis using currently known tests depends on the skill and experience of the clinician. A misdiagnosis can lead to unnecessary delay in treatment, thereby placing the patient at increased risk for further damage to the knee.

There are manual tests for the LCL, MCL and the PCL. Each manual test relies on grading the extent of the ligament lengthening into three categories. There is no effort to grade the compliance of the ligament; however, the expert clinician will describe the ligament in terms of its 'feel'. The more ligaments and structures that are damaged; the more complex it becomes to perform a knee examination using the subjective manual exams.

There have been multiple attempts in the past to instrument the knee and quantify or measure the change in the structure of the knee after ligament damage. Only one device has attempted to accurately quantify the extent or relative displacement and compliance a ligament in the knee. The KT-1000 and the KT-2000 Medmetric® measure the anterior-posterior translation of the tibia with respect to the femur along the z-axis. These devices attempt to quantify the findings found when the clinician uses the Lachman's test and the Anterior Drawer Test. Force is applied to a handle on the device which measures force and signals to the clinician the amount of force with a low pitched sound for the 15 pound force, a higher pitched sound for the 20 pound force. This force pulls anteriorly along the z-axis through a strap that wraps underneath the calf. The measurement of the translation uses a technique measuring the relative motion of a pad on the anterior tibia with respect to a pad placed on the patella. This device does not measure relative displacement or compliance in any of the other degrees of freedom previously described in the knee. Furthermore, the quantified results of the KT-1000 or KT-2000 have not been correlated with patient satisfaction where as the subjective Pivot Shift test has bee correlated with patient satisfaction.

Accordingly, there is a need for an accurate, objective, reliable and reproducible measure of the impact of damage to the ACL as well as other ligaments and structures in the knee that can be used in the clinical setting on patients. For example, since an injury to the ACL produces both an increase in anterior translation (z-axis translation) and rotation (y-axis rotation), an objective measure of these changes would both aid in the diagnosis of the injury as well as verify its restoration after ligament reconstruction surgery. Additionally, measurement of displacement and compliance around different degrees of freedom in the knee would help objectively describe the individual and complex changes to 'joint play' that occur with an injury to the knee. A need exists for systems and methods that can provide accurate, reproducible and objective data on the changes in 'joint play' that occur with an injured knee compared to their normal knee and to the population as a whole such that the clinician can achieve patient satisfaction with focused, biomechanical and proven surgical interventions individualized for that injury and for that knee across the entire population of damaged knees.

Needs also exist for systems and methods, and devices which accommodate variances of patient body structure; it may well be understood that each human body is different and may require particular attention when being treated and/or analyzed; this may be particularly evident in the case of abnormalities of bone, tendon, joint, etc., due to injury or the like.

BRIEF SUMMARY OF THE INVENTION

Generally described, the present invention to provide apparatuses and methods for evaluating the performance of joints and their associated elements.

One aspect of the present invention provides a limb and joint measurement apparatus and system capable of providing information relating to the following: joint range of motion, stability, laxity, and compliance. Various methods of measuring joint range of motion, stability, laxity, and compliance in six degrees of freedom (three angular and three linear) are provided and contemplated.

Another aspect of the present invention provides a limb and joint measurement apparatus and system capable of accommodating a patient's "natural alignment", which could vary from one limb to the other and from patient to patient; the adjustability feature accommodates such accommodation for said natural alignment.

Another aspect of the present invention contemplates positioning the user in such natural alignment such that certain variances between legs, joints, can be accommodated, particularly the valgus/varus alignment of the knee.

Other aspects, features, and advantages of the present invention will become apparent upon reading the following detailed description of the preferred embodiment of the invention when taken in conjunction with the drawing and the appended claims.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 1:
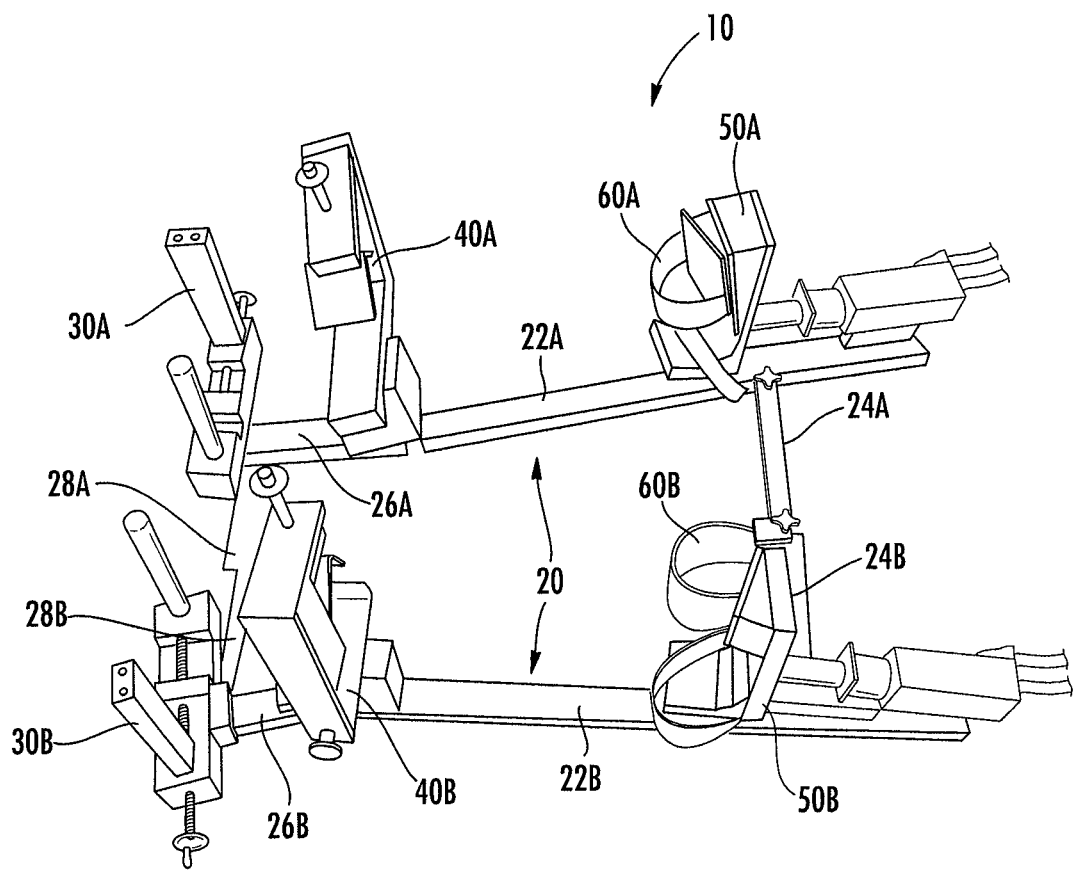
FIG. 1 is a perspective view of the apparatus 10 according to the present invention. Shown are a frame 20, two primary rails 22A and 22B, two secondary rails 26A and 26B, two femur stabilizer assemblies 30A and 30B, two patella stabilizer assemblies 40A and 40B, two rotation assemblies 50A and 50B, and two foot support assemblies 60A and 60B.

FIG. 11 is a side view of an apparatus 100 according to the present invention. Also shown are a primary rail 122, a secondary rail 126, a leg support 143, a leg 2, and a torsion device T.

Figure 12:
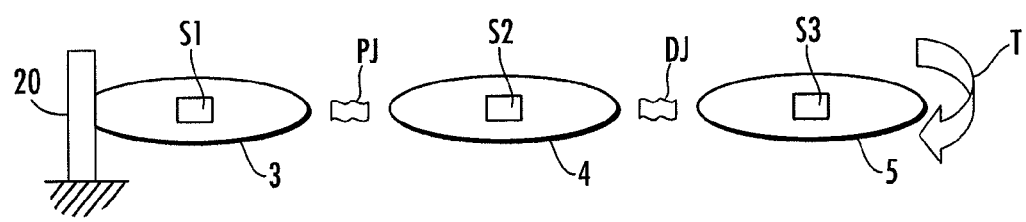

FIG. 12 is a schematic diagram depicting a set of sensors S1, S2, and S3 that monitor and evaluate movement of a thigh 3, a lower leg 4, and a foot 5 relative to one another as a torque T is applied according to the present invention. Also shown are a proximal joint PJ and a distal joint DJ.

Figure 13:
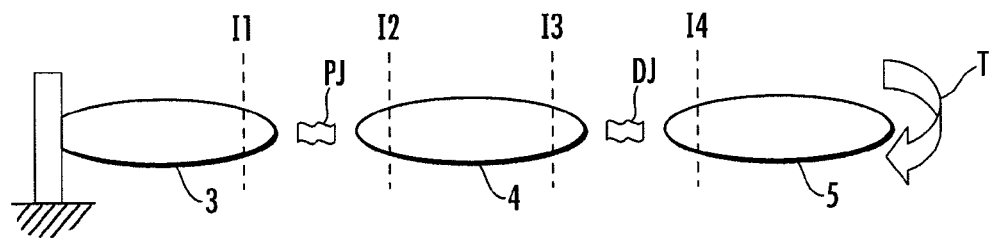

FIG. 13 is a schematic diagram depicting a set of images I1, I2, I3, and I4 that monitor and evaluate movement of a thigh 3, a lower leg 4, and a foot 5 relative to one another as a torque T is applied according to the present invention. Also shown are a proximal joint PJ and a distal joint DJ.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Generally described, various embodiments of the present invention provide devices and methods for evaluating the knee, although other joints and limbs can likewise be evaluated such as the elbow and arm. In one aspect of the invention, a device is provided which applies a known torque to the lower leg of a user and monitors the reaction to this torque at the knee. In various embodiments, the user's femur and ankle are stabilized such that the movement of the tibia at the knee in response to a given torque can be accurately measured.

In various embodiments of the present invention, the torque is applied by a computer controlled motor. The computer may be programmed to instruct the motor to perform any desired diagnostic routine. For example, the diagnostic routine may comprise rotating the user's lower leg in a clockwise direction from a neutral position until a predetermined threshold is reached and then back to neutral. This procedure may be repeated for 3 cycles. Then, the user's leg may be rotated from a neutral position in a counterclockwise until a predetermined threshold is reached and back to neutral for three cycles. In another example, the diagnostic routine may comprise the rotating of a user's lower leg in a clockwise direction until a predetermined threshold is met and then rotate the in a clockwise direction until a predetermined threshold is met in a substantially fluid motion. This procedure may be repeated for several cycles. Clockwise and counterclockwise rotations can be made in either the x, y, or z axes, by placing the motor in different orientations.

In various embodiments, both of the user's lower legs may be rotated simultaneously. For example, the user's left leg may be rotated counter clockwise (external rotation) and then clockwise (internal rotation) while the user's right leg is rotated clockwise (external rotation) and then counter clockwise (internal rotation). By rotating the legs simultaneously in opposite directions, the movement in the hip area can be minimized since the motions counter act each other. This allows evaluation of not only two limbs simultaneously, but also both joints of both limbs (e.g. two knees and two ankles).

While the diagnostic routine is performed, various parameters may be monitored to evaluate the performance of the knee. In one embodiment, angle of rotation and torque measurements are taken at regular intervals during the diagnostic routine. From this data, a hysteresis curve can be generated, which may be used to evaluate the performance of the knee. In another embodiment, a flock of birds measuring technique is used to monitor the movement of the tibia during the diagnostic routine. In this embodiment, a sensor is positioned proximate the knee of the patent and aligned substantially with the tibia. As torque is applied to the user's lower leg, this device monitors movement of the tibia in response to the applied torque. The movement may be correlated with the torque applied in order to evaluate the knee's performance. More detailed measurement techniques are described elsewhere in this application.

Bilateral Joint Evaluation Apparatus 10

Various embodiments of the present invention provide methods and apparatuses for accurately measuring the rotational performance of a knee. FIG. 1 illustrates a bilateral joint evaluation apparatus 10 in accordance with an embodiment of the present invention.

ELEMENT LIST

02 Leg
03 Thigh
04 Lower leg
05 Foot
06 Femur
07 Patella
08 Tibia
PJ Proximal Joint
DJ Distal Joint
10 Apparatus
20 Frame
22A, B Primary Rails
23A, B Distal Carriages
24A, B Distal Cross Members
25 Locking Mechanism
26A, B Secondary Rails
27A, B Proximal Carriages
28A, B Proximal Cross Members
29 Locking Mechanism
30A, B Femur Stabilizer Assemblies
33A Support Bar
34A, B Inside Thigh Stabilizers
35A, B Outside Thigh Stabilizers
36A,B Threaded Rods
37A Locking Mechanism
38A Locking Mechanism
40A, B Patella Stabilizer Assemblies
41A Locking Mechanism
42A Base
43A,B Leg Supports
44A,B Support Columns
45A,B Support Beams
46A,B Patella Stabilizers
47A,B Adjustment Bars
48A,B Fine Adjustment Mechanisms
49A Locking mechanism
50A, B Rotation Assemblies
53A Support Column
54A Bracket
55A Shaft
56A, B Motors
57A Coupling
60A,B Foot Support Assemblies
62A Base Plate
64A Heel Support
66A Sole Plate
67A Hinge
70A Dorsiflexion Wedge
72A Inflatable Dorsiflexion Bladder
73A Pronation Plate
74A Pronation Wedge
76A Ankle Strap
78A Metatarsal Strap
100 Second Apparatus
122 Primary Rail
126 Secondary Rail
143 Leg Support
S1 First Sensor
S2 Second Sensor
S3 Third Sensor
I1 First Image
I2 Second Image
I3 Third Image
I4 Fourth Image General Operation of Apparatus 10

The apparatus 10 includes a frame 20, two femur stabilizer assemblies 30A,B, two patella stabilizer assemblies 40A,B and two rotation assemblies 50A,B. In practice, a user is positioned into the device with each foot secured to a rotation assembly 50A,B. The patella stabilizer assemblies 40A,B restrict movement of the patella and as a result also restrict to some degree the movement of the user's femurs. The femur stabilizer assemblies 30A,B further secure the user's thighs. Generally, the patella stabilizer assemblies and the femur stabilizer assemblies restrict movement of the femur such that movement of the user's lower leg in response to a torque applied through the rotation assemblies is substantially transferred to the tibia.

Frame 20

Figure 2:
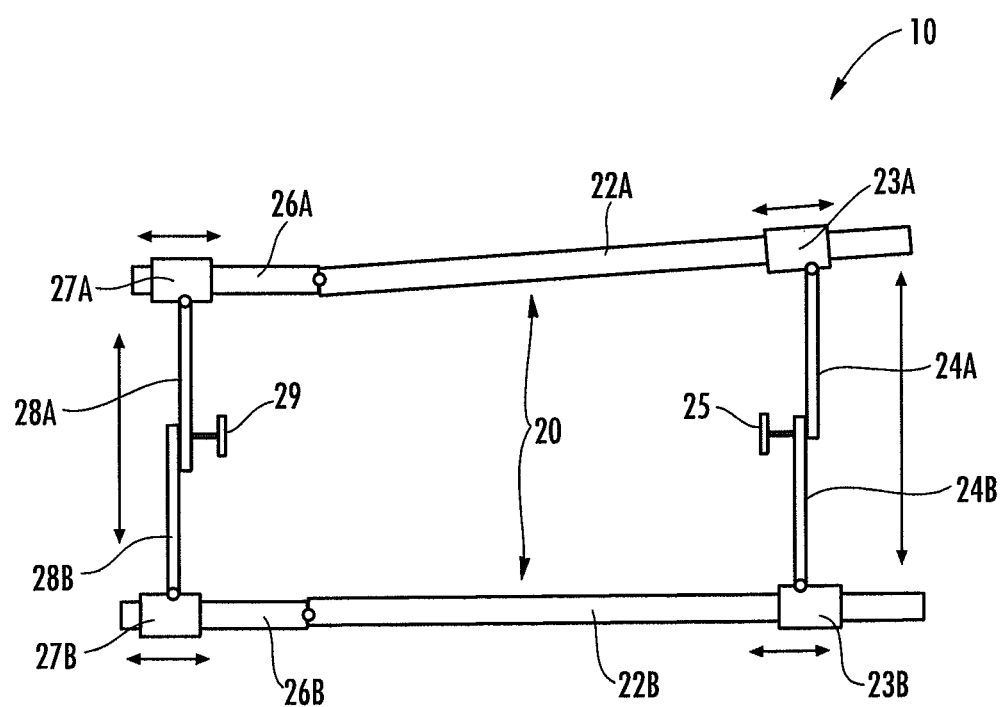
FIG. 2 is a schematic diagram of the frame 20 according to the present invention. Also shown are two distal carriages 23A and 23B, two proximal carriages 27A and 27B, two distal cross members 24A and 24B, and two proximal cross members 28A and 28B.

FIG. 2 provides a schematic diagram of the frame 20. Generally, the frame 20 is configured to be positioned atop a supporting surface such as a table, the floor or other substantially horizontal surface. The frame 20 includes two primary rails 22A,B, two secondary rails 26A,B, two proximal carriages 27A,B, two proximal cross members 28A,B, two distal carriages 23A,B and two distal cross members 24A,B. In the illustrated embodiment, primary rail 22A and secondary rail 26A are positioned end to end and are pivotably connected relative to one another. Likewise, primary rail 22B and secondary rail 26B are also positioned end to end and are pivotably connected to one another. In use, the primary rails 22A,B are substantially aligned with the user's right and left tibias, respectively. Similarly, the secondary rails 26A,B are substantially aligned with the user's right and left femurs or thighs, respectively. The pivoting connections between the primary and secondary rails allow the device to be adjusted for users having legs in a varus or valgus condition. It should be noted that the primary rails may or may not be parallel with each other or with the corresponding secondary rails.

Figure 6:
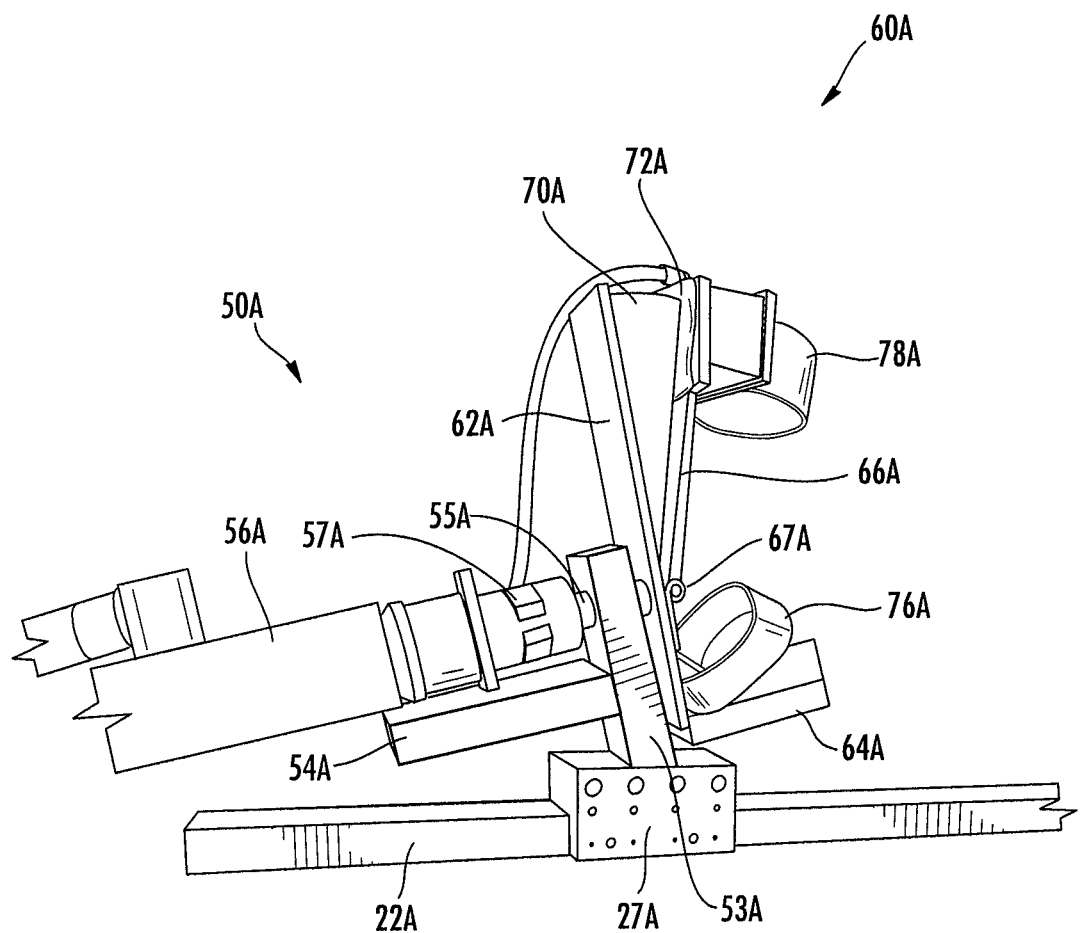
FIG. 6 is a detailed perspective view of the rotation assembly 50A and the front support assembly 60A according to the present invention. Also shown are a support column 53A, a base plate 62A, a heel support 64A, and a sole plate 66A.

The distal carriages 23A,B are slidably connected relative to the primary rails 22A,B, respectively, such that the distal carriages can travel along at least a portion of the length of the primary rails 22A,B as generally indicated in FIG. 2. In the illustrated embodiment, the distal carriages 23A,B, slide independently from one another. In addition, the distal carriages each include a locking mechanism (not shown) that allows the carriages to be selectively secured relative to its respective primary rail at a desired location. As will be discussed in greater detail later, the distal carriages 23A,B provide a mounting location for the rotation assemblies 50A,B as can be seen in FIG. 6.

Distal carriage 23A is connected to distal carriage 23B by distal cross members 24A,B. Cross member 24A is pivotably connected to distal carriage 23A at one end and slideably connected to distal cross member 24B near the other end. Similarly, distal cross member 24B is pivotably connected to distal carriage 23B at one end and slideably connected to cross member 24A proximate the other end. In the illustrated embodiment, a locking mechanism 25 may selectively secure the distal cross members 24A,B to each other at a desired location. As will be discussed in greater detail later, the slideable connection of the two cross members 24A,B allow the free ends of the primary rails to adjusted closer together or farther away as generally indicated in FIG. 2.

The proximal carriages 27A,B are slidably connected relative to the secondary rails 26A,B, respectively, such that the distal carriages 23 A,B can travel along at least a portion of the length of the secondary rails 26A,B as generally indicated in FIG. 2. In the illustrated embodiment, the proximal carriages 27A,B slide independently from one another. In addition, the proximal carriages 27A,B each include a locking mechanism (not shown) that allows the carriages to be selectively secured relative to its respective secondary rail at a desired location. As will be discussed in greater detail later, the proximal carriages 27 A,B provide a mounting location for the thigh stabilizer assemblies 30A,B as can be seen in FIG. 3.

Proximal carriage 27A is connected to proximal carriage 27B by proximal cross members 28A,B. Cross member 28A is pivotably connected to proximal carriage 27A at one end and slideably connected to cross member 28B near the other end. Similarly, proximal cross member 28B is pivotably connected to proximal carriage 27B at one end and slideably connected to proximal cross member 28A near the other end. In the illustrated embodiment, a locking mechanism 29 may be selectively engaged to secure proximal cross members 28A,B to each other at a desired location. As will be discussed in greater detail later, the slideable connection of the two cross members 24A,B allows the free ends of the primary rails to adjusted closer together or farther away as generally indicated in FIG. 2.

Femur Stabilizer Assembly 30 (a.k.a., Proximal Stabilizer Assembly)

Figure 3:
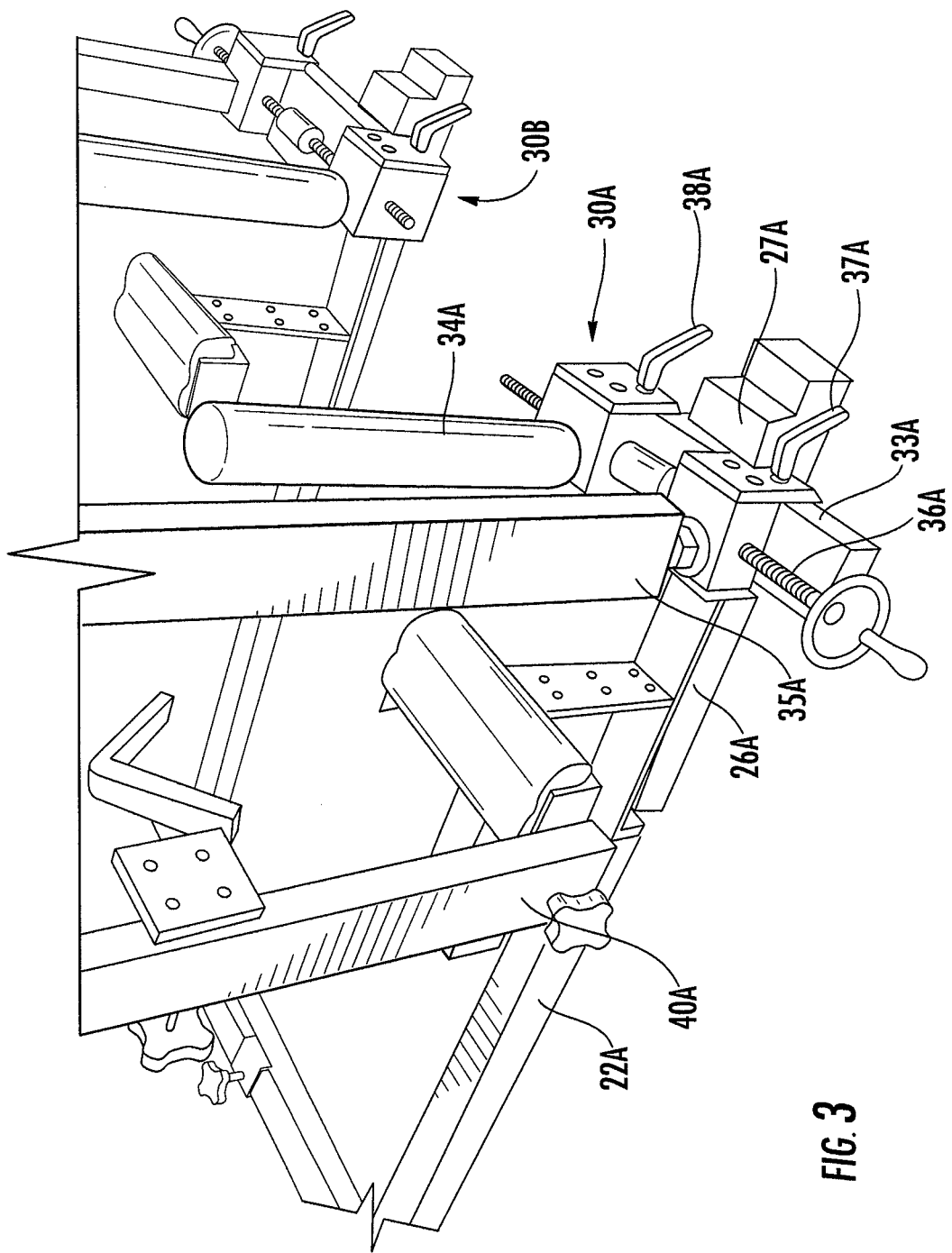
FIG. 3 is a detailed perspective view of the femur stabilizer assembly 30A according to the present invention. Also shown are an inside thigh stabilizer 34A and an outside thigh stabilizer 35A.
Figure 4:
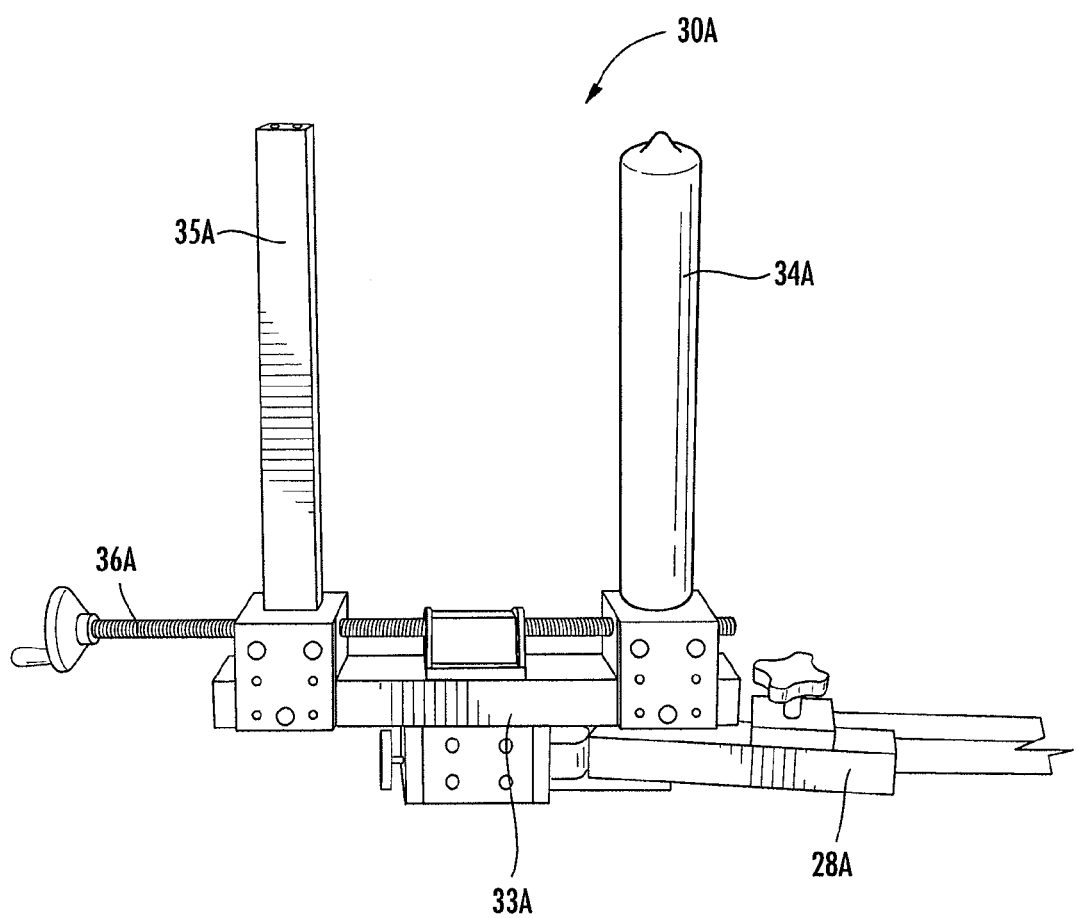
FIG. 4 is a detailed front view of the femur stabilizer assembly 30A according to the present invention. Also shown are a support bar 33A, the inside thigh stabilizer 34A, the outside thigh stabilizer 35A, and a threaded rod 36A.

FIGS. 3 and 4 illustrate an exemplary femur stabilizer assembly 30A in accordance with an embodiment of the present invention. Generally described, the femur stabilizer assemblies 30A,B are designed to minimize movement of the femur 6B(a.k.a., proximal segment) in response to a torque T applied to the rotation assemblies 50A,B. As mentioned above, the bilateral joint evaluation apparatus 10 includes two femur stabilizer assemblies 30A,B, one for each leg 2 (a.k.a., limb).

The following paragraphs generally describe femur stabilizer assembly 30A; however it should be understood that femur stabilizer assembly 30B is configured substantially the same. The femur stabilizer assembly 30A includes a support bar 33A, an inside thigh stabilizer 34A, an outside thigh stabilizer 35A and a threaded rod 36A.

The support bar 33A is rigidly connected relative to the proximal carriage 27A and is oriented substantially perpendicular to the secondary rail 26A. Slideably attached relative to the lateral side of the support bar 33A is the outside thigh stabilizer 35A, which is an elongate component that has a substantially rectangular cross section. In other embodiments, the outside thigh stabilizer 35A may have a different cross section such as a circle, a triangle, or square. The outside thigh stabilizer 35A extends upwardly and substantially perpendicularly from the support bar 33A and is configured to pivot about its elongate axis in relation to the support bar 33A. In use, the outside thigh stabilizer is configured to be positioned on the lateral (i.e. outside) side of the user's respective thigh 3. A locking mechanism 37A may be provided that is configured to selectively lock the outside thigh stabilizer 35A at a desired location in relation to the support bar 33A.

The inside thigh stabilizer 34A is slideably attached to the medial side of the support bar 33A such that it can travel along at least a portion of the elongate length of the support bar 33A. The inside thigh stabilizer 34A is an elongate component that has a substantially circular cross section, which extends upwardly substantially perpendicularly from the support bar 33A. In other embodiments, the inside thigh stabilizer 34A may have a different cross section such as a triangle, rectangle or square. In use, the inside thigh stabilizer 34A is configured to contact the medial (i.e. inside) of the user's respective thigh. A locking mechanism 38A may also be provided to selectively lock the inside thigh stabilizer in relation to the support bar 33A as desired.

In practice, the inside thigh stabilizer 35A and the outside thigh stabilizer 34A work together to stabilize the thigh 3 of a user. More specifically, the two stabilizers are spaced apart to receive a user's thigh therebetween. The two stabilizers 34A and 35A are operatively connected to the threaded rod 36A such that they slide linearly along the support bar 33A when the rod is turned. Generally described, the threaded rod 36A includes right-handed threads on one end of the rod which are engaged by to one of the stabilizers and left-handed threads on the other end of the rod, which are engaged by the other stabilizer. Therefore, when the threaded rod 36A is turned, the stabilizers move in different linear directions. For example, when the threaded rod 36A is turned a first direction (e.g., clockwise), the two stabilizers 34A and 35A slide along the support bar 33A toward each other thereby squeezing the user's thigh 3 therebetween. When the threaded rod is turned in a second direction (e.g., counterclockwise), the two stabilizers 34A and 35A move away from each other. In various embodiments, the pitch of the right-handed threads and the left-handed threads are the same such that the two stabilizers move the same linear distance in response to a single turn.

Patella Stabilizer 40A,B (a.k.a., Proximal Joint Stabilizing Assembly)

A shown in FIG. 1, the bilateral joint evaluation apparatus 10 includes two patella stabilizer assemblies 40A,B, (a.k.a., knee or proximal joint stabilizer assemblies) one for each leg. The following paragraphs generally describe patella stabilizer assembly 40A; however it should be understood that patella stabilizer assembly 40B is configured substantially the same.

Figure 5:
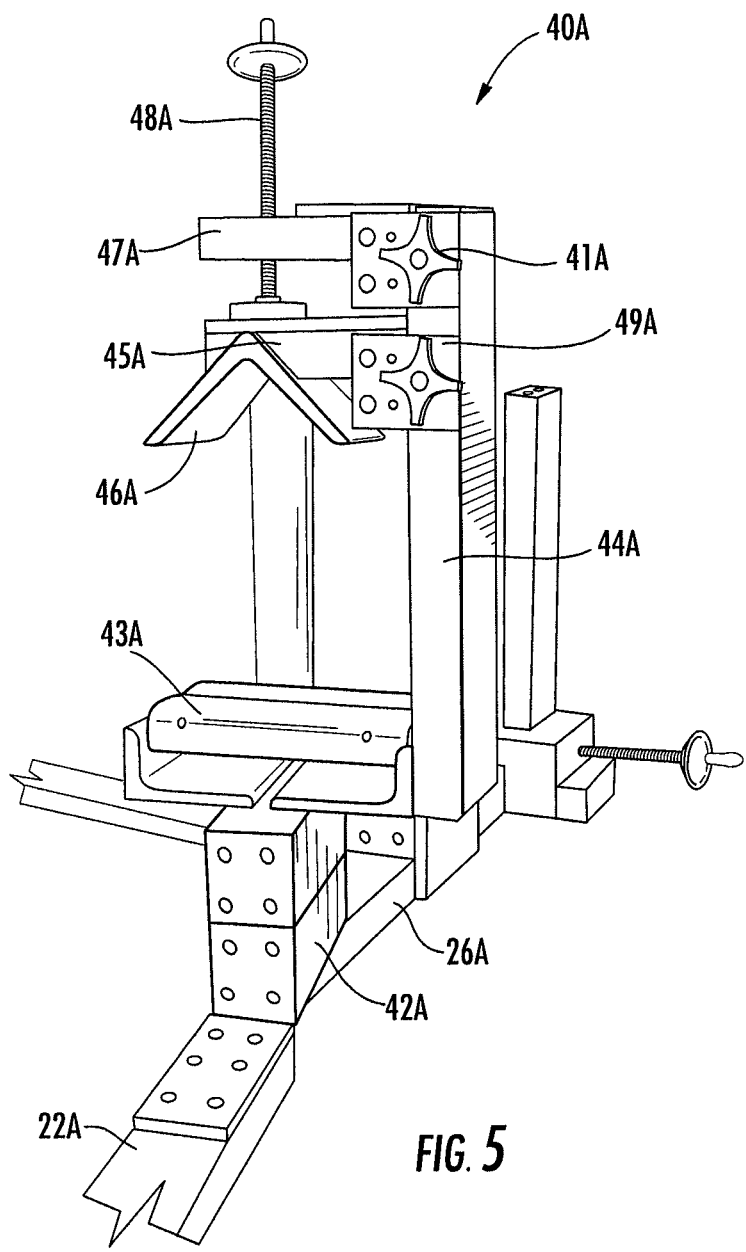
FIG. 5 is a detailed perspective view of the patella stabilizer assembly 40A according to the present invention. Also shown are a leg support 43A, a support beam 45A, a patella stabilizer 46A, and a fine adjustment mechanism 48A.

As illustrated in FIG. 5, the patella stabilizer assembly 40A includes a base 42A, a leg support 43A, a support column 44A, a V-shaped patella stabilizer 46A, a support beam 45A, an adjustment bar 47A and a fine adjustment mechanism 48A. Generally described, the patella stabilizer 40A is configured to restrict movement of the patella such that movement of the lower leg in response to a torque applied to the rotation assembly 50A is substantially isolated in the tibia.

The base 42A of the patella stabilizer 40A assembly is rigidly attached proximate the end of the primary rail 22A near the secondary rail 26A. Attached to the base 42A in a perpendicular orientation is the leg support 43A. The leg support 43A has a generally elongate structure and is configured to aid in positioning the leg of a user in a bend condition. For the comfort of the user, the leg support 43A may have rounded edges and may also be padded. The leg support 43A optionally may also be adjustable up and down as shown later in FIG. 11.

Extending upwardly from the leg support 44A is the support column 44A. This component is substantially elongate.

Slideably attached to the support column 44A is the support beam 45A. The support beam 45A extends over the leg support 43A and is oriented substantially parallel thereto. In the illustrated embodiment, a locking mechanism 49A is provided, which is configured to selectively resist movement of the support beam 45A with respect to the support column 44A. The V-shaped patella stabilizer 46A is rigidly attached proximate the end of the support beam 45A and the "V" is substantially aligned with the primary rail 22A and is positioned such that the "V" opens toward the leg support 44A.

Positioned above the V-shaped patella stabilizer 46A is the adjustment bar 47A and the fine adjustment mechanism 48A. Generally, the adjustment bar 47A is slideably attached to the support column 44A and is substantially parallel with the support beam 45A. A locking mechanism 41A is provided such that the adjustment bar 47A can be selectively locked relative to the support column 44A.

In the illustrated embodiment, the adjustment mechanism 48A is a threaded rod, which is operatively attached to the adjustment bar 47A such that as the rod is turned, a force may be applied to the top of the V-shaped patella stabilizer 46A and/or the support beam 45A.

Rotation Assemblies 50A,B (a.k.a., Distal Stabilizer Assembly)

A shown in FIG. 1, the bilateral joint evaluation apparatus 10 includes two rotation assemblies 50A,B, one for each leg. The following paragraphs generally describe rotation assembly 50A; however it should be understood that rotation assembly 50B is configured substantially the same.

FIG. 6 illustrates a rotation assembly 50A in accordance with an embodiment of the present invention. Generally described, the rotation assembly 50A includes support column 53A, a bracket 54A, a shaft 55A, a motor 56A, a coupling 57A and a foot support assembly 60A. The column 53A in one embodiment is rigidly attached to the carriage 27A, which itself is slideably connected to the primary rail 22A. The column 53 extends upwardly at an angle approximately 60 degrees from horizontal. The column 53A supports both the motor 56A and the foot support assembly 60A. The motor 56A is secured to the column 53A by bracket 54A and is positioned such that the motor 56A is operatively connected to a first end of the shaft 55A via coupling 57A. As will be understood by those of skill in the art, the coupling 57A may provide a safety mechanism such that torque exceeding a predetermine threshold is not transferred from the motor 56A to the shaft 55A.

The shaft 55A extends through and may be supported by a bushing positioned the column 53A. The second end of the shaft 55A is rigidly connected to the foot support assembly 60A. The shaft 55A is generally attached at a location on the foot support assembly 60A such that the shaft 55A will be in substantial alignment with the tibia 8 of a user when the apparatus is in use.

In the illustrated embodiment, the motor 56A and the shaft 55A are in substantial alignment with the primary rail 22A and the motor and shaft are also tilted upward at an approximate angle of 30 degrees from the horizontal. As mentioned earlier, the shaft will be in substantial alignment with the tibia of a user that has his or her knee bent at approximately 30 degrees.

Optionally, the support column 53A could be adjustable to allow the relative height of the motor and shaft to be adjusted to ensure proper torque application in line with the patient's limb in accordance with the degree of proximal joint flexion fixed by the leg support 43A. In addition, the motor and shaft may be attached to either side and/or top of the footplate in order to provide rotation about the x and z axes.

As may be seen, each rotation assembly operates in association with a foot support assembly, with the combination being a foot support and rotation assembly.

Foot Support Assembly 60A,B (a.k.a., Distal Segment Support Assembly)

A shown in FIG. 1, the bilateral joint evaluation apparatus 10 includes two foot (a.k.a., distal member) support assemblies 60A,B, one for each leg. The following paragraphs generally describe foot support assembly 60A; however it should be understood that foot support assembly 60B is configured substantially the same. As noted above, each foot support assembly operates in association with a rotation assembly 50 A,B, with the combination being a foot support and rotation assembly.

Referring to FIG. 6, the foot support assembly 60A is rigidly attached to the second end of the shaft 55A and is configured in one embodiment and use to minimize relative movement of the foot relative to the tibia. In other words, the ankle is immobilized such that torque applied to the rotation assemblies 50A is transferred to the tibia with minimal influence by the ankle. The foot support assembly 60A includes a base plate 62A, a V-shaped heel support 64A, a sole plate 66A, a hinge 67A, a dorsiflexion wedge 70A and an inflatable dorsiflexion bladder 72A. The base plate 62A is a substantially planar component with a substantially rectangular shape that is rigidly attached to the end of the shaft 55A such that the plane formed by the base plate 62A is substantially perpendicular to the axis of the shaft 55A. The V-shaped heel support 64A is rigidly attached proximate the lower end of the base plate 62A such that the "V" opens upwardly.

The sole plate 66A is attached to the base plate 62A via hinge 67A. The sole plate 66A is positioned on the same side of the base plate 62A as the V-shaped heel support. The axis of the hinge 67A is substantially perpendicular to the axis of the shaft 55A and is attached to the base plate 62A at a location above the V-shaped heel support 64A.

The dorsiflexion wedge 70A is in one embodiment substantially rigid and positioned between the base plate 62A and the sole plate 66A such that in use, the user's foot will be held in dorsiflexion. The illustrated embodiment 70A holds the user's foot in approximately 15 degrees of dorsiflexion.

The inflatable dorsiflexion bladder 72A is positioned between the dorsiflexion wedge 70A and the sole plate 66A to provide additional dorsiflexion as desired. Specifically, the dorsiflexion bladder 72A may be inflated thereby causing the sole plate 66A to pivot about the hinge 67A so that a user's foot is positioned in additional dorsiflexion.

Figure 7:
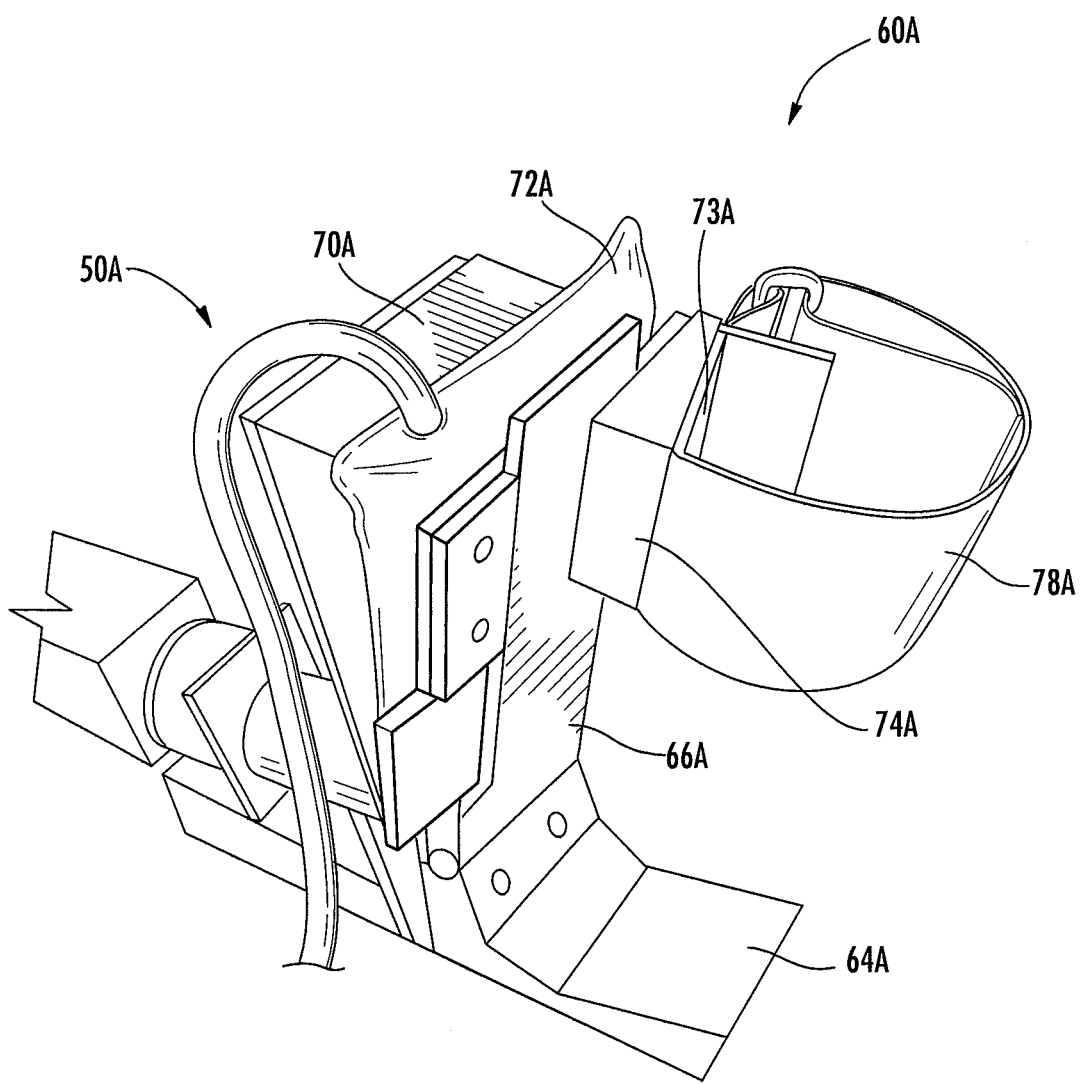
FIG. 7 is a detailed perspective view of the rotation assembly 50A and the front support assembly 60A according to the present invention. Also shown are a dorsiflexion wedge 70A, an inflatable dorsiflexion bladder 72A, a pronation plate 73A, and a pronation wedge 74A.

FIG. 7 provides a top view of the foot support assembly 60A. In addition to the dorsiflexion wedge 70A and the dorsiflexion bladder 72A, a pronation wedge 74A is also provided. The pronation wedge 74A is rigidly connected to the pronation plate 73A, which is slideably connected to the sole plate 66A. The pronation wedge 74A is in one embodiment adjustable in its angle, either by replacement with differing wedges, or by use of an inflation feature. One purpose of the pronation wedge 74A is to twist the foot inwardly to minimize relative movement between the foot and the tibia. Another purpose in another method of use embodiment is to accommodate the patient's natural alignment, which could vary from one leg to the other and from patient to patient; the adjustability feature accommodates such accommodation for said natural alignment. As noted elsewhere, the present invention also contemplates positioning the user in such natural alignment such that certain variances between legs, joints, can be accommodated. This accommodation for said natural alignment feature is likewise true for the dorsiflexion wedge and bladder, which could also be used independently of each other. Such natural alignment characteristics also will vary from user to user; one aspect of the inventive concepts referenced herein accommodates different patients.

Figure 8:
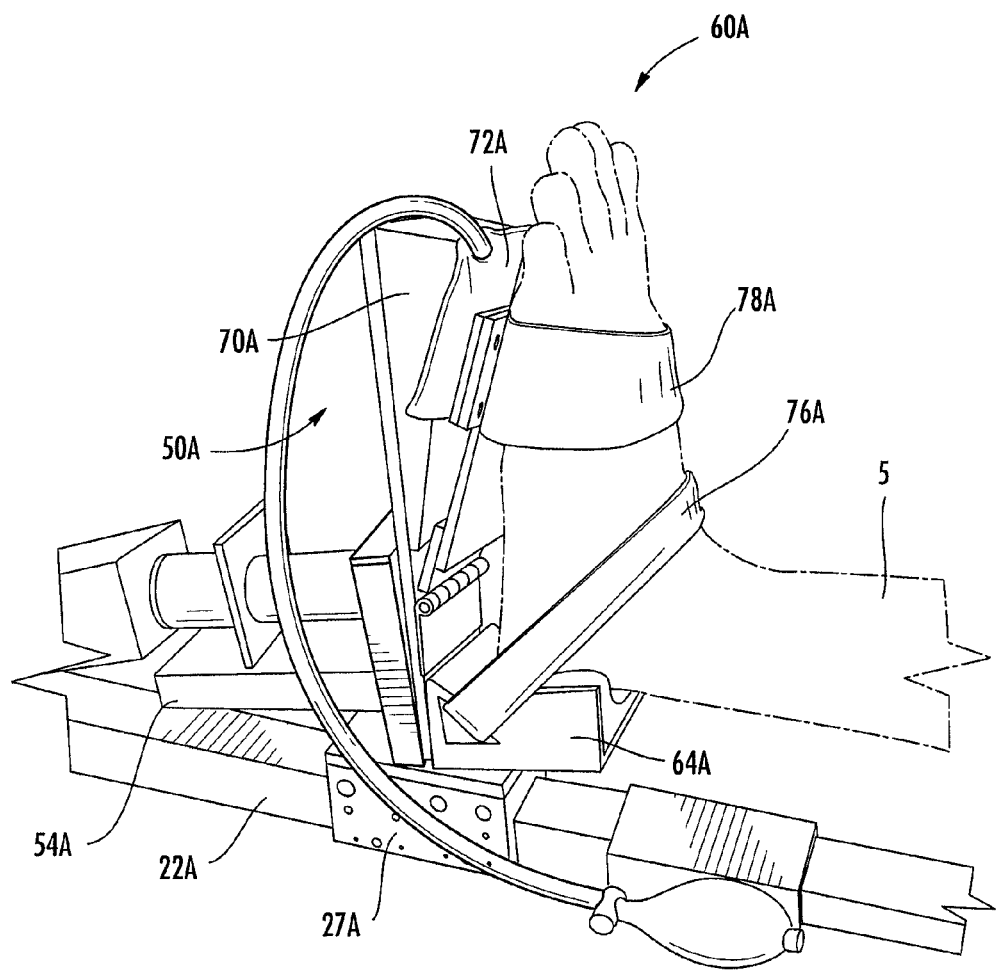
FIG. 8 is a detailed perspective view of the rotation assembly 50A and the front support assembly 60A according to the present invention. Also shown are a foot 5, a metatarsal strap 78A, and an ankle strap 76A.

FIG. 8 illustrates how the foot support assembly 60A secures the foot 5 of a user. As illustrated, the user's heel is positioned in the "v" of the V-shaped heel support and the bottom of the foot is in contact with the sole plate. An ankle strap 76A urges the user's heel into the V-shaped heel support 64A and a metatarsal strap 78A urges the user's foot against the sole plate and the pronation wedge (not shown).

The dorsiflexion wedge and bladder could be used in combination as shown but without the use of the pronation plate. Furthermore, either of the dorsiflexion wedge and bladder could be used alone and without the pronation plate.

It may thus be seen that the apparatus is attached to various portions of the leg. Such attachment is done by baising against the leg, such that multiple attachment locations capture the leg.

Methods of Use

In various embodiments of the present invention, methods are provided for evaluating the performance of the knees of a user. The following paragraphs generally describe exemplary methods of evaluating a user's knees.

One Method

In one exemplary method according to various embodiments of the present inventions, the first step in evaluating a user's knees is to minimize the influence of other joints when evaluating the reaction of the knees to a given torque applied proximate the foot. Initially, the user is positioned supine with the user's thighs positioned in the femur stabilizer assemblies 30A,B of a bilateral joint evaluation apparatus 10 and the user's knees are positioned in the patella stabilizer assemblies 40A,B. Specifically, each thigh is positioned between an associated inside thigh stabilizer 34A,B and an outside thigh stabilizer 35A,B. Also, the user's knees are positioned between the respective leg supports 43A,B and V-shaped patella stabilizers 46A,B. The patella stabilizers 40A,B are then adjusted such that the V-shaped patella stabilizer 43A,B engages the user's knee cap. This process includes sliding the support beams 45A,B such that the V-shaped patella stabilizers contact the respective knees of the users. Next, the adjustment bars 47A,B are slid toward the support beams 45A,B such that the fine adjustment mechanisms 48A,B contact the support beams 45A,B. The adjustment bars 47A,B are then locked in place using a locking mechanism 41A,B. A predetermined torque is then applied to the fine adjustment mechanisms 48A,B such that the V-shaped patella stabilizers 43A,B are urged against the user's respective knees. Once the predetermined torque has been applied, the support beams 45A,B are locked relative to the support columns 44A,B by the locking mechanisms 49A,B.

After positioning the user in the apparatus 10 and urging the V-shaped patella stabilizer against the respective knees of the user, the secondary rails 26A,B are generally aligned with the user's thighs and the primarily rails 22A,B are generally aligned with the user's tibias. The rotation assemblies 50A,B are then slid forward along primary rails 22A,B and the user's feet are positioned in the respective foot support assemblies 60A,B. In one use embodiment, the foot is then positioned on the sole plates 66A,B according to the patient's natural ankle alignment. The alignment of the foot and ankle are then fixed by using the adjustable dorsiflexion and pronation wedges either individually or in concert. At this point, the three-dimensional position of each segment and joint of the lower extremity has been appropriately matched to the patient's natural alignment or posture. The system is then calibrated and the positions of each segment and each joint are recorded as the patient's static or natural starting position.

Next, the ankle straps 76A,B are be tightened against the user's respective feet. The pronation plates 73A,B are then slid along the sole plates 66A,B until they are positioned proximate the top of the metatarsals of the user's respective feet and the metatarsal straps 78A,B tightened for each respective foot are tightened. Once the user's feet are secured to the foot support assemblies 60A,B, the distal cross members 24A,B are locked in place to discourage movement of the primary rails 22A,B.

The next step is to secure the thighs of the user to the device. As mentioned earlier, the user's thighs are positioned between the respective inside thigh stabilizers 34A,B and outside thigh stabilizers 35A,B. The first step is to slide the carriages 27A,B along the secondary rails to a desired location and to lock them in place relative to the secondary rails 22A,B. Next, the threaded rods 36A,B are turned such that the inside thigh stabilizers 34A,B and outside thigh stabilizers 35A,B are urged toward the thighs positioned therebetween. In one embodiment, the inside and outside thigh stabilizers move toward each other at the same rate and squeeze the thigh therebetween. As a result of the stabilizers moving at the same rate and the pivoting attachment of the secondary rails 26A,B to the primary rails 22A,B, the secondary rails 26A,B will substantially align themselves with the respective thighs. In one embodiment, a predetermined torque is applied to the threaded rod.

After the thighs have been secured by the femur stabilizer assemblies 30A,B, the proximal cross members 28A,B are locked together. At this point, the user is ready for the application of a torque to his or her knees.

Once the user has been secured by the thigh stabilizer assemblies 30A,B, the patella stabilizer assemblies 40A,B and the rotation assemblies 50A,B, rotational data can be gathered. In various embodiments of the present invention, a computer or other programmable controller is configured to control the motors 56A,B to perform a desired diagnostic routine. For example, the diagnostic routine may comprise repeating several cycles of rotating the user's foot support assemblies 60A,B in a first direction (e.g., clockwise) from a neutral position (i.e. the foot pointing substantially upward) until a predetermined threshold is reached. Next, the user's leg may be rotated in a second direction (e.g., counterclockwise) from the neutral position until a predetermined threshold is reached for three cycles.

In other embodiments, the diagnostic routine may comprise the rotating of a user's lower leg in a clockwise direction until a predetermined threshold is met and then rotate the in a clockwise direction until a predetermined threshold is met in a substantially fluid motion. This procedure may be repeated for several cycles.

In various embodiments, both of the user's lower legs may be rotated in simultaneously. For example, the user's left leg may be rotated counter clockwise (external rotation) and then clockwise (internal rotation) while the user's right leg is rotated clockwise (external rotation) and then counter clockwise (internal rotation). By rotating the legs simultaneously in opposite directions, the movement in the hip area can be minimized since the motions counter act each other. In other embodiments, the rotation of each leg may be performed independently.

Figure 9:
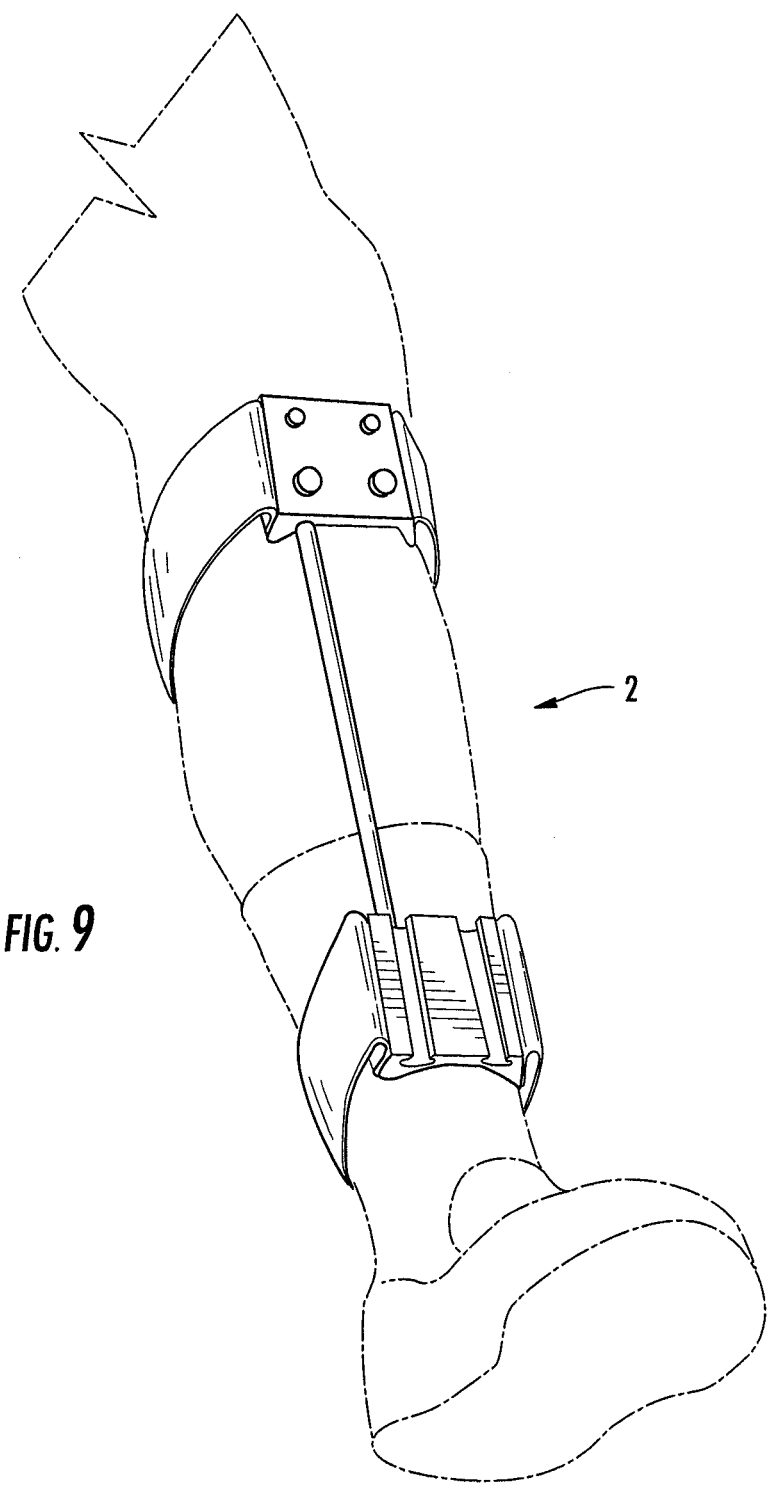
FIG. 9 is an illustrative view of a device that monitors and evaluates the performance of a patella 7 when placed in the apparatus 10 according to the present invention.
Figure 10:
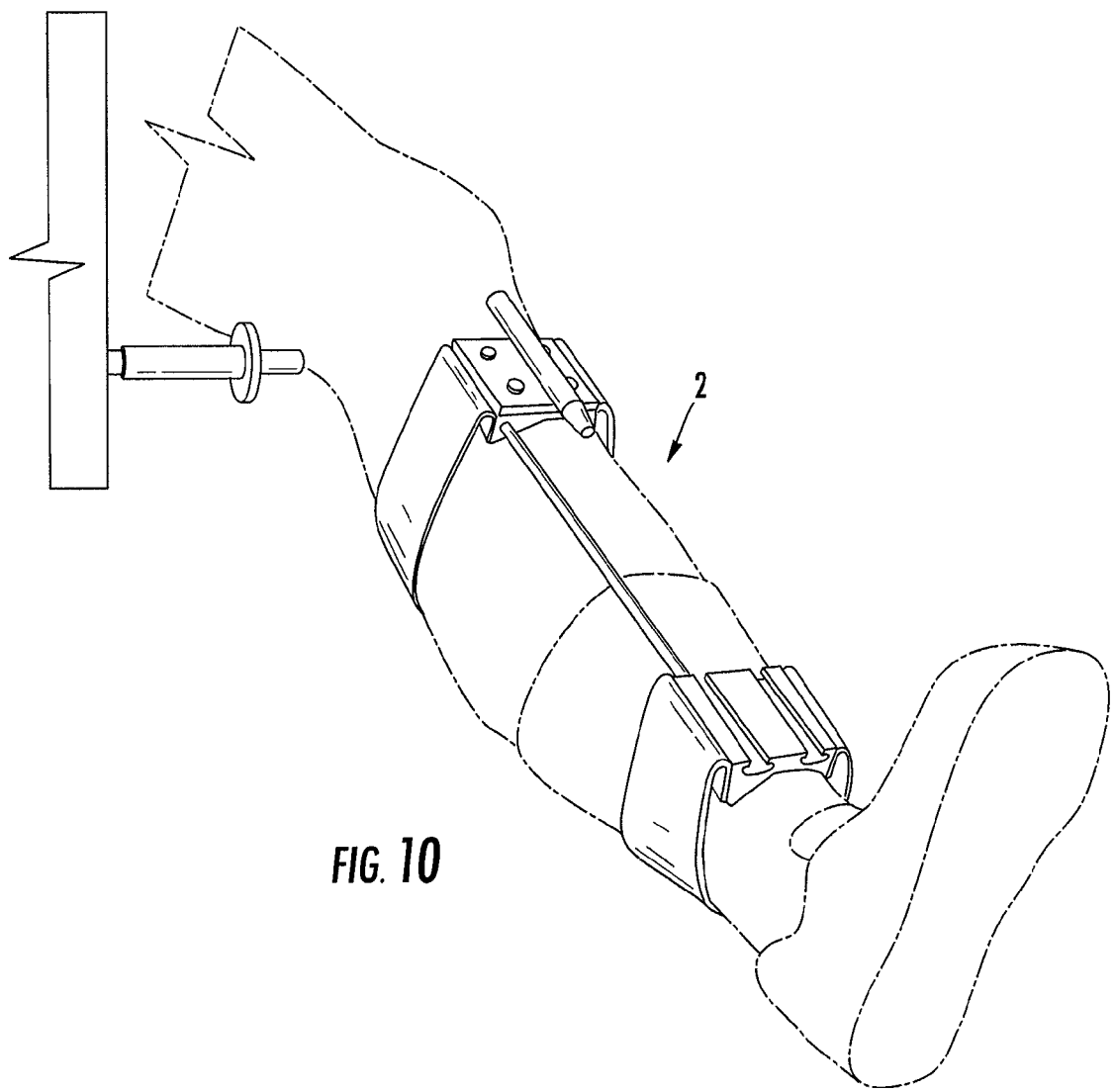
FIG. 10 is an illustrative view of a flock of birds sensor that monitors and evaluates the performance of a patella 7 when placed in the apparatus 10 according to the present invention.
Figure 17:
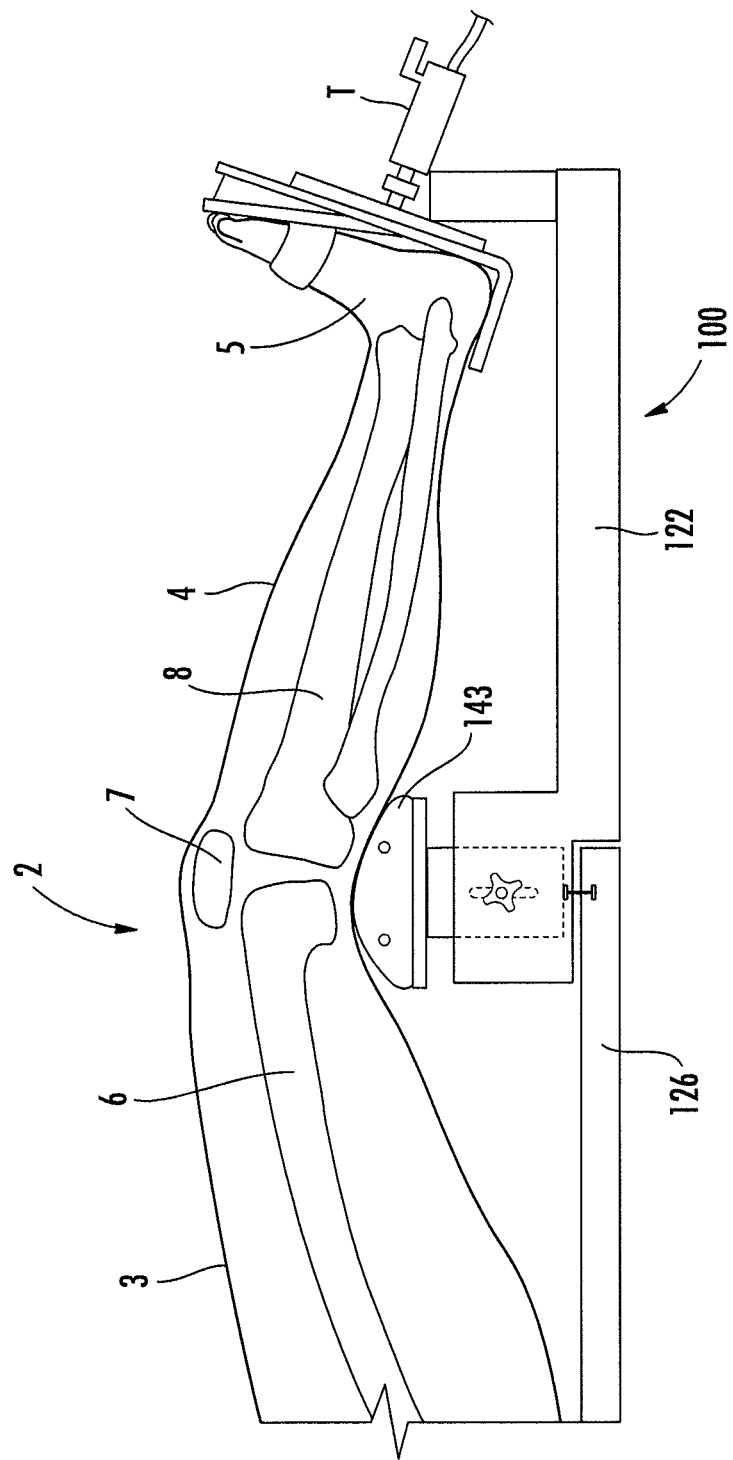

While the diagnostic routine is performed, various parameters may be monitored to evaluate the performance of the knee. In one embodiment, angle of rotation and torque measurements are taken at regular intervals during the diagnostic routine. From this data, a hysteresis curve can be generated, which may be used to evaluate the performance of the knee. In another embodiment, a flock of birds measuring technique is used to monitor the movement of the tibia during the diagnostic routine. In this embodiment, a sensor is positioned proximate the knee of the user (See FIGS. 9 and 10) and aligned substantially with the tibia. As torque is applied to the user's lower leg, this device monitors movement of the tibia in response to the applied torque. The movement may be correlated with the torque applied in order to evaluate the knee's performance.

Advantages of Method

As may be seen, the positioning apparatus 10 above has a pivot point located below each knee flexion platform. The pivot (also included in another apparatus shown below) allows the both the thigh and lower leg to be positioned correctly for the patient's natural valgus/varus alignment of the knee. By allowing to be adjusted for valgus/varus alignment, testing can be performed on each patient with the ligaments and other knee structures tensioned according to each patient's natural knee alignment. By not correcting for valgus/varus alignment, and thus forcing the knee into a straight alignment or an alignment that is unnatural for that patient, the ligaments and other knee structures could be inappropriately or unequally tensioned prior to and during testing, thus creating error in the measures of knee range of motion, stability, laxity, and compliance.

Once the valgus/varus alignment and knee flexion angle have been fixed, the Patella Stabilizing Assembly is positioned if the clinician desires to control the relative position of the patella. If the clinician desires to evaluate the knee with the patella allowed to move (for example in order to evaluate the patellofemoral joint), under one embodiment of one of the inventions the Patella Stabilizing Assembly will not be used in order to evaluate the patellofemoral joint. When and if the Patella Stabilizing Assembly has been positioned, the Proximal Stabilizing Assembly can be used to control the position of the thigh.

Other Apparatuses and Methods of Use

Other apparatuses and methods included under the present invention are now also discussed.

Apparatus 100

Reference is now made to FIG. 11, which is an illustrative view of a portion of an apparatus 100 used in association with an exemplary patient leg 2 (a.k.a., "limb"), said leg including a thigh 3 (a.k.a., "proximal segment"), a lower leg 4 (a.k.a., "intermediate segment"), a foot 5 (a.k.a., "distal segment"), a femur 6 (part of the proximal segment), a patella 7, and a tibia 8 (part of the intermediate segment).

Apparatus 100 is another embodiment of an invention described herein, which as may be seen includes a frame 20, an exemplary primary rail 122 (one of two assuming a bilateral apparatus 100 is contemplated), and an exemplary secondary rail 126 (one of two assuming a bilateral apparatus 100 is contemplated). An exemplary leg support 143 (one of two assuming a bilateral apparatus 100 is contemplated) is also included. The rails 122 and 126 function similarly to the previously described corresponding rails 22 and 26, however the leg support 143 is adjustable vertically (in the orientation shown) to provide for a variation in the bending of the knee as needed.

Thus it may be seen that the above configuration, as does the apparatus 10 configuration, provides a method and apparatus for reliably positioning a 3-segment limb, such as a leg or arm for imaging and medical analysis. The apparatus positions the limb in such a way that the position of the proximal segment 3 (thigh or upper arm) is controlled while a known external torque is applied at a known rate to the distal segment 5 (foot or hand). The location of each of the limb's three segments can then be recorded using either external or internal measurement techniques, and the relative motions between the proximal and intermediate segments 4 (thigh and lower leg, upper arm and forearm) are used in the orthopedic evaluation of the proximal joint (knee or elbow). Furthermore, the relative motions between the intermediate and distal segments (lower leg and foot, forearm and hand) are used in the orthopedic evaluation of the distal joint (ankle or wrist). By applying a known torque at a known rate, clinicians will be provided with valuable information related to joint range of motion, stability, laxity, and compliance. This information can be collected on a single joint or may be collected simultaneously on two joints and two limbs.

Further Discussion of Methods—Accommodation of Patient's Natural Alignment

It may be understood that the apparatuses and methods described herein accommodate for the patient's "natural alignment" which for purposes of this discussion means the relative configuration of the particular patient involved, as opposed to a "typical, healthy, one-size-fits-all" model. In many situations, patients may have small or large variations from the "norm", such as being bow-legged, "knock-kneed" or the like. Furthermore, one of the patient's legs may have a different shape or other characteristic compared to the other, for a myriad of reasons. The configurations and methods described herein can accommodate such variations, by the various adjustments described herein. As may be seen, the present inventions accommodate the patient's natural alignment.

Patients are positioned supine with the knee joint resting on a leg support 143. The height of the leg support 143 can be adjusted to control the amount of knee flexion during testing. As with apparatus 10, the apparatus 100 has a pivot point located below the knee flexion location. The pivot allows the both the thigh and lower leg to be positioned correctly for the patient's natural alignment, in this case the patient's natural valgus/varus alignment of the knee. By allowing to be adjusted for valgus/varus alignment, testing can be performed on each patient with the ligaments and other knee structures tensioned according to each patient's natural knee alignment. By not correcting for valgus/varus alignment, and thus forcing the knee into a straight alignment or an alignment that is unnatural for that patient, the ligaments and other knee structures could be inappropriately or unequally tensioned prior to and during testing, thus creating error in the measures of knee range of motion, stability, laxity, and compliance.

Once the valgus/varus alignment and knee flexion angle have been fixed, the Patella Stabilizing Assembly of apparatus 100 is positioned if the clinician desires to control the relative position of the patella. If the clinician desires to evaluate the knee with the patella allowed to move, the Patella Stabilizing Assembly will not be used. When and if the Patella Stabilizing Assembly has been positioned, the Proximal Stabilizing Assembly will be used to control the position of the thigh. This same variation of use or nonuse of the Patella Stabilizing Assembly can likewise be used in conjunction with the use of the apparatus 10.

If desired the footplate can be moved along the bottom rail 22A to adjust to the patient's leg length. The foot is then positioned on the footplate according to the patient's natural ankle alignment. The alignment of the foot and ankle are then fixed by using the adjustable dorsiflexion and pronation wedges either individually or in concert. At this point, the three-dimensional position of each segment and joint of the lower extremity has been appropriately matched to the patient's natural alignment or posture. The system is then calibrated as needed so that the positions of each segment and each joint are recorded as the patient's static or natural starting position. This process can be used with either apparatuses 100 or 10.

Note that the dorsiflexion and pronation wedges (either individually or in concert) are used in order to either 1) flex and/or twist the foot inwardly to minimize relative movement between the foot and the tibia, or to 2) simply accommodate the patient's natural alignment. In the second instance the wedges and any adjment thereof can simply be done in order to attempt to accommodate such alignment and in fact could be done to position the ankle to maximize relative movement between the foot and the tibia.

A torque T is then applied to the footplate with a computer-controlled motor. The motor controls both the amount of torque applied and the rate at which it is applied. The system provides torque first in one direction until the desire torque threshold is reached. The system then reverses the direction of the torque until the torque threshold is reached in the opposite direction. The system performs at least one complete cycle to precondition the ligaments and other structures of the limb prior to testing. After the final preconditioning cycle, the footplate returns to a position at which the motor senses that zero torque is required to maintain the position. The system then records that position as it may provide useful information to the clinician about the patient's knee and/or ankle. This process can be used with either apparatuses 100 or 10.

After preconditioning, the system then initiates the testing sequence. The motor again applies at least one cycle of torque in positive and negative directions, and information about the position and orientation of the three segments are recorded using either the external or internal measurements systems. The relative positions and orientations of the three segments are then used to determine the relative joint motion in six degrees of freedom. Another unique aspect of this system is that since the position, orientation, amount of torque, rate of torque application, and the rate of joint motion are known, all aspects of joint range of motion, stability, laxity, and compliance can be determined, recorded, displayed and generated in a format for storage purposes by the software we have created. This process can be used with either apparatuses 100 or 10.

This testing can be performed on a single limb or on both limbs simultaneously, and data measured and joint characteristics calculated can be determined for a single joint or for any combination of both knees and ankles of the two limbs. Furthermore, the torque can be applied in multiple cycles, and in multiple sets of cycles. Multiple test repetitions and sets allow for further descriptive data to be generated such as averages, variability of measures, and range of values recorded. This applies to either apparatuses 100 or 10.

Particular Measurement Techniques

Reference is now made to FIG. 12, which is an illustrative view illustrating an exemplary limb such as leg 2 shown in FIG. 11 positioned using an apparatus 10 or 100 as described above, with the proximal segment fixed relative to the exemplary frame portion 20. As may be seen, the leg also includes a proximal joint PJ intermediate the proximal segment 3 and the intermediate segment 4. Localizing sensors S1, S2, and S3 are placed on each of the limb's three corresponding segments 3, 4, and 5. An external torque T (relative to the frame 20) is then applied to the distal segment causing motion of both the distal and intermediate segments. Localizing Sensors S1 and S2 provide the location of each corresponding segment in space (there may be some movement between the proximal segment 3 and the frame 20, said movement which is recognized by the sensor S1), and the relative motion between the proximal and intermediate segments 3, 4, is recorded and can be used to record, process, generate, and display information about the range of motion, stability, laxity, and compliance of the proximal joint (e.g., a knee or elbow joint). Also, the localizing Sensors S2 and S3 provide the location of the intermediate and distal segments 4, 5, in space, and the relative motion between the intermediate and distal segments 4, 5, can be used to record, process, generate, and display information about the range of motion, stability, laxity, and compliance of the distal joint DJ (e.g., an ankle or wrist joint).

The localizing sensors can include electromagnetic tracking devices which locate their three-dimensional position and orientation in respect to an electromagnetic field emitter, opto-electronic tracking devices which emit optical signal which are received by a camera, said camera enabled to follow the three-dimensional position of each sensor, and/or ultrasonic devices which locate their three-dimensional position and orientation with respect to one another.

Reference is now made to FIG. 13, which is an illustrative view illustrating an exemplary limb such as leg 2 shown in FIG. 11 positioned using an apparatus 10 or 100 as described above, with the proximal segment fixed relative to the exemplary frame portion 20. As may be seen, the leg also includes a proximal joint PJ intermediate the proximal segment 3 and the intermediate segment 4. The exemplary limb such as leg 2 is first positioned using the apparatus as shown in FIGS. 1 or 11 above, and the patient is placed in the gantry of an imaging device, such as a CT or MR scanner, or other radiographic or fluoroscopic imaging device.

An external torque T (relative to the frame 20) is then applied to the distal segment 5 causing motion of both the distal and intermediate segments. At set time intervals, captured two or three dimensional images I1, I2, I3, and I4 are captured of the distal aspect of the proximal segment 3 (thigh or upper arm) and the proximal aspect of the intermediate segment 4 (lower leg or forearm). Sequentially evaluating the relative positions between the two segments then allows the determination of relative motion of the proximal joint (e.g., knee or elbow), as well as to record, process, generate, and display information about joint range of motion, stability, laxity, and compliance of the proximal joint PJ (e.g., knee or elbow). Also, the images can be captured of the distal aspect of the intermediate segment and the proximal aspect of the distal segment. Sequentially evaluating the relative positions between the two segments then allows the determination of relative motion of the distal joint DJ (e.g., ankle or wrist), as well as to record, process, generate, and display information about range of motion, stability, laxity, and compliance of the distal joint (ankle or wrist). It should be understood that non-metallic or other appropriate materials should be used as needed in order to avoid conflict with the scaning devices.

Conclusion

Thus are methods and apparatus for reliably positioning a 3-segment limb, such as a leg or arm for imaging and medical analysis, which can accommodate for the patient's "natural alignment". The apparatus positions the limb in such a way that the position of the proximal segment (thigh or upper arm) is controlled while an known external torque is applied at a known rate to the distal segment (foot or hand). The location of each of the limb's three segments is recorded using either external or internal measurement techniques, and the relative motions between the proximal and intermediate segments (thigh and lower leg, upper arm and forearm) are used in the orthopedic evaluation of the proximal joint (knee or elbow). Furthermore, the relative motions between the intermediate and distal segments (lower leg and foot, forearm and hand) are used in the orthopedic evaluation of the distal joint (ankle or wrist). By applying a known torque at a known rate, clinicians will be provided with valuable information related to joint range of motion, stability, laxity, and compliance. This information can be collected on a single joint or may be collected simultaneously on two joints and two limbs.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for evaluating leg movement characteristics of a patient having a particular valgus/varus knee condition, said patient having a first leg including a first upper leg portion and a first lower leg portion, a first knee between said first upper and lower leg portions, and a first foot, said patient having a second leg including a second upper leg portion and a second lower leg portion, a second knee between said second upper and lower leg portions, and a second foot, said apparatus comprising:
   a frame assembly, said frame assembly comprising:
   1) a first lower leg supporting portion comprising a first primary rail, said first lower leg supporting portion being configured for attachment to said first lower leg portion, said first lower leg supporting portion including a foot rotation assembly comprising a foot support member configured to support said first foot of said patient and to selectively attach relative to said first foot, said foot rotation assembly being configured to exert a force upon said foot support member to provide rotation of said first foot relative to said first primary rail and to transfer a torque to the first knee of said patient;
   2) a first upper leg supporting portion comprising a first secondary rail, said first upper leg supporting portion being configured for attachment to said first upper leg portion, said first secondary rail pivotably attached relative to said first primary rail by an intermediate pivoting connection comprising at least one pivot axis configured to extend through said first knee, said first upper leg supporting portion configured to support said first upper leg separately from said first lower leg supporting portion, said intermediate pivoting connection being configured to pivot about said at least one pivot axis to accommodate a patient's particular valgus/varus knee condition;
   3) a second lower leg supporting portion comprising a second primary rail;
   4) a second upper leg supporting portion comprising a second secondary rail pivotably attached relative to said second primary rail to allow for variation in a particular patient's valgus/varus knee condition when said apparatus is in use by said patient;
   5) a distal cross member having two opposing ends, a first of the two opposing ends being pivotably attached relative to said first primary rail, a second of the two opposing ends being pivotably attached relative to said second primary rail; and
   6) a proximal cross member having two opposing ends, a first of the two opposing ends being pivotably attached relative to said first secondary rail, a second of the two opposing ends being pivotably attached relative to said second secondary rail.

2. The apparatus of claim 1, further comprising:
   a second foot rotation assembly for selective attachment relative to said second foot and for rotating said second foot relative to said second primary rail;
   a first patella stabilizer assembly for selective attachment relative to said first leg proximate a first patella and for fixing said first patella relative to said first primary rail;
   a second patella stabilizer assembly for selective attachment relative to said second leg proximate a second patella and for fixing said second patella relative to said second primary rail;
   a first femur stabilizer assembly for selective attachment relative to said first leg proximate said first femur and for fixing said first femur relative to said first secondary rail; and
   a second femur stabilizer assembly for selective attachment relative to said second leg proximate said second femur and for fixing said second femur relative to said second secondary rail.

3. The apparatus of claim 2, further comprising first and second distal carriages slidably adjustable along the lengths of first and second primary rails, respectively, and wherein said first and second foot rotation assemblies are rigidly mounted to said first and second distal carriages, respectively, such that said first and second foot rotation assemblies may be adjusted relative to the lengths of said first and second primary rails, respectively.

4. The apparatus of claim 2, wherein said secondary rails are elongate, and wherein said selective attachment of each of said femur stabilizers relative to corresponding said femurs is provided by an adjustment device that tends to maintain alignment of the axis of said secondary rail with said corresponding femur as said adjustment device is tightened onto said leg proximate said corresponding femur.

5. The apparatus of claim 2, wherein said distal cross member is elongate between said two opposing ends and comprises an adjustable locking mechanism configured such that a distance can be adjusted, said distance being that between: (1) said pivoting connection of said first of the two opposing ends relative to said first primary rail; and (2) said pivoting connection of said second of the two opposing ends relative to said second primary rail.

6. The apparatus of claim 2, wherein said proximal cross member is elongate between said two opposing ends and comprises an adjustable locking mechanism configured such that a distance can be adjusted, said distance being that between: (1) said pivoting connection of said first of the two opposing ends relative to said first secondary rail; and (2) said pivoting connection of said second of the two opposing ends relative to said second secondary rail.

7. The apparatus of claim 2, wherein said first and second foot rotation assemblies further are each configured to provide rotation of said respective foot by exerting a torque upon said foot, and further comprising separate measurement devices configured to measure each said torque.

\* \* \* \* \*